(12) United States Patent
Wang et al.

(10) Patent No.: US 11,965,995 B2
(45) Date of Patent: Apr. 23, 2024

(54) MULTI-PHYSICAL FIELD IMAGING METHOD AND SYSTEM BASED ON PET-CT AND DAS

(71) Applicant: Institute of Geology and Geophysics, Chinese Academy of Sciences, Beijing (CN)

(72) Inventors: Yibo Wang, Beijing (CN); Zizhuo Ma, Beijing (CN); Yikang Zheng, Beijing (CN); Shaojiang Wu, Beijing (CN); Qingfeng Xue, Beijing (CN)

( * ) Notice: Subject to any disclaimer, the term of this patent is extended or adjusted under 35 U.S.C. 154(b) by 0 days.

(21) Appl. No.: 18/321,746

(22) Filed: May 22, 2023

(65) Prior Publication Data

US 2023/0296797 A1 Sep. 21, 2023

(30) Foreign Application Priority Data

Sep. 14, 2022 (CN) .......................... 202211112376.2

(51) Int. Cl.
*G01T 1/29* (2006.01)
*A61B 5/00* (2006.01)
(Continued)

(52) U.S. Cl.
CPC .......... *G01T 1/2985* (2013.01); *G01N 23/046* (2013.01); *G01N 29/14* (2013.01);
(Continued)

(58) Field of Classification Search
CPC .... G01T 1/2985; G01N 23/046; G01N 29/14; G01N 29/227; G01N 2223/1016;
(Continued)

(56) References Cited

U.S. PATENT DOCUMENTS

| 2012/0223235 | A1* | 9/2012 | Maucec | ............... G01N 15/082 |
| | | | | 250/362 |
| 2015/0159471 | A1* | 6/2015 | Jones | ...................... E21B 43/28 |
| | | | | 166/302 |

(Continued)

FOREIGN PATENT DOCUMENTS

| CA | 2860575 C | * | 9/2018 | |
| CN | 105928793 A | * | 9/2016 | ............... G01N 3/12 |

(Continued)

OTHER PUBLICATIONS

CN202211112376 Notice of Allowance; The State Intellectual Property Office of the People's Republic of China dated Dec. 14, 2022; p. 1; Beijing, China.

(Continued)

*Primary Examiner* — Mischita L Henson
*Assistant Examiner* — Monica S Young
(74) *Attorney, Agent, or Firm* — Addison D. Ault; Richard P. Moerschell; IPGentleman Intellectual Property Services, LLC

(57) ABSTRACT

Embodiments of the present disclosure provide a multi-physical field imaging method based on PET-CT and DAS, comprising: wrapping distributed acoustic sensors on a surface of a non-metallic sample to be tested, and then placing them in a pressure device; loading triaxial pressures; preparing a tracer fluid; pumping the tracer fluid into the non-metallic sample; collecting PET images and CT images of internal structure of the non-metallic sample, meanwhile, monitoring internal acoustic emission events of the non-metallic sample in real time; combining the PET images with the CT images, to obtain PET/CT images; locating the acoustic emission events, and obtaining occurrence time and spatial location of internal structural perturbations; and analyzing a mechanism of fluid-solid coupling effect in the non-metallic sample under loaded stress. The imaging (Continued)

method and system of the present disclosure can accurately and reliably image the fluid-solid coupling process in the material.

10 Claims, 3 Drawing Sheets

(51) Int. Cl.
   *G01N 21/17* (2006.01)
   *G01N 23/046* (2018.01)
   *G01N 29/14* (2006.01)
   *G01N 29/22* (2006.01)

(52) U.S. Cl.
   CPC .......... *G01N 29/227* (2013.01); *A61B 5/0095* (2013.01); *G01N 21/1702* (2013.01); *G01N 2021/1704* (2013.01); *G01N 2223/1016* (2013.01); *G01N 2223/108* (2013.01); *G01N 2223/311* (2013.01); *G01N 2223/419* (2013.01); *G01N 2223/616* (2013.01)

(58) Field of Classification Search
   CPC ....... G01N 2223/108; G01N 2223/311; G01N 2223/419; G01N 2223/616; G01N 29/2418; G01N 29/2431; G01N 2223/508; G01N 21/1702; G01N 2021/1704; G01N 29/2425; A61B 5/0095
   USPC .......................................................... 73/825
   See application file for complete search history.

(56) References Cited

U.S. PATENT DOCUMENTS

| | | | |
|---|---|---|---|
| 2017/0032532 A1* | 2/2017 | Andersen | G01N 23/04 |
| 2018/0306736 A1* | 10/2018 | Li | G01N 23/046 |
| 2019/0250294 A1* | 8/2019 | Salman | G06N 3/08 |
| 2019/0265373 A1* | 8/2019 | Ito | E21B 17/025 |

FOREIGN PATENT DOCUMENTS

| | | | | |
|---|---|---|---|---|
| CN | 105954104 A | * | 9/2016 | ............. G01N 23/04 |
| CN | 105973702 A | * | 9/2016 | ........... G01N 23/046 |
| CN | 206074355 U | * | 4/2017 | |
| CN | 107462190 A | * | 12/2017 | |
| CN | 108240942 A | * | 7/2018 | ............... G01N 3/06 |
| CN | 111157557 A | * | 5/2020 | ........... G01N 23/046 |
| CN | 115201235 A | * | 10/2022 | |

OTHER PUBLICATIONS

CN202211112376 Notice of Allowance; The State Intellectual Property Office of the People's Republic of China dated Dec. 14, 2022; p. 1; Beijing, China (English translation).
CNIPA Office Action, Application No. CN202211112376.2, dated Nov. 14, 2022, pp. 1-8.
CNIPA Office Action, Application No. CN202211112376.2, dated Nov. 14, 2022 (English Translation, downloaded from Global Dossier on Jul. 19, 2023) pp. 1-11.
Ma, Z., et al., In situ dynamic X-ray imaging of fluid-rock interactions inside tight sandstone during hydraulic fracturing: fluid flow process and fracture network growth. J Petroleum Science and Engineering, vol. 214 (2022) 110490, Apr. 15, 2022, pp. 1-11.

* cited by examiner

MULTI-PHYSICAL FIELD IMAGING METHOD AND SYSTEM BASED ON PET-CT AND DAS

CROSS-REFERENCE TO RELATED APPLICATION

This application claims priority to Chinese Patent Application No. 202211112376.2, filed on Sep. 14, 2022 before the China National Intellectual Property Administration, the disclosure of which is incorporated herein by reference in entirety.

TECHNICAL FIELD

The present disclosure relates to the field of image data processing or generation, in particular, the disclosure relates to image analysis using PET-CT technology, especially, a multi-physical field imaging method and system based on PET-CT and DAS. The multi-physical field imaging method and system of the present disclosure combine PET-CT and DAS, and DAS utilizes Rayleigh backward scattering (RBS) S) in an optical fiber to locate and recover mechanical vibration information (amplitude, phase and frequency) at anywhere on the optical fiber, therefore it also belongs to the field of mechanical vibration measurement, specifically, the application of radiation-sensitive devices such as optical devices to measure mechanical vibration.

BACKGROUND

Fluid-solid coupling problems widely exist in nature and many practical projects, for example, there are surface subsidence problems that are caused by groundwater pumping or oil and gas reservoir exploitation, there are dam stability problems that are caused by water reservoir storage, there are pollution diffusion problems that are caused by underground storage of nuclear waste, there are leakage problems of carbon dioxide geological storage, and there are earthquake induction problems that are caused by hydraulic fracturing exploitation of unconventional oil and gas, hydraulic fracturing exploitation of enhanced geothermal power, exploitation of salt mine, wastewater reinjection and other constructions.

The key to study the fluid-solid coupling effect focuses on the process of change of the internal structure and state of the medium material under the action of the fluid. Non-destructive detection technology of opaque medium materials has been widely applied in the industrial field. Both active source ultrasound tomography and acoustic emission tomography are effective means to monitor the change of the internal structure and state of the materials. The experiment of simulating materials in different mechanical scenarios in small-scale laboratories is the most direct and common way to study the fluid-solid coupling effect of various materials. In such kind of experiments, the mechanical conditions can be flexibly set according to different experimental scenarios. Meanwhile, it is convenient to carry out multi-physical field monitoring work, obtaining monitoring data of multi-parameter physical quantities, and helping to carry out a comprehensive analysis of the fluid-solid coupling effect of the materials.

Generally, the experimental objects to be studied are mostly opaque non-metallic materials, and it is impossible for the naked eye to directly observe the change of the internal structure and state of the materials during the experiment. Traditional interior active source ultrasonic tomography or acoustic emission tomography monitoring generally adopts monitoring probes arranged on the surface of the sample to be tested, to indirectly monitor the change of the internal structure of the sample to be tested during the experiment, and then adopts inversion calculation, to indirectly obtain the occurrence of structural perturbations under the action of the internal fluid-solid coupling of the materials. Generally, the scale of the adopted experimental samples is small, and the error in calculation accuracy of the inversion algorithm itself will significantly affect the reliability of the calculation results, and affect the accurate description of the fluid-solid coupling phenomenon in the materials. This is a deficiency of the current experimental imaging methods.

PET-CT technology is a nuclear medicine monitoring method that combines positron emission tomography (PET) technology and CT imaging technology. PET imaging adopts radioactive positron nuclide tracers to obtain internal molecular information of the sample to be tested, and provides images of the tracer distribution in the sample. CT imaging directly images the internal structure of the material based on the difference in the X-ray absorption degree of various parts of the sample to be tested with different internal density. By combining PET imaging results with CT imaging results, high-precision and high-resolution imaging effects can be obtained. At present, PET/CT technology is not limited to the application in the field of medical imaging, but can also be applied to high-precision imaging of the internal structure of materials.

Distributed Acoustic Sensing (DAS) technology is a new type of acoustic sensing technology developed rapidly along with the development of optical fiber communication technology. Its principle is as follows: utilize Rayleigh backward scattering (RBS) in an optical fiber to locate and recover the mechanical vibration information (amplitude, phase and frequency) anywhere on the optical fiber, detect and locate strain signals occurring anywhere on the optical fiber, and obtain strain signal waveform linearly. Optical fiber has the advantages of intrinsic safety, resistance to electromagnetic interference, and resistance to harsh environments, and has a wide range of applications. The phase-sensitive optical frequency domain reflectometer (d)-OFDR), as a distributed acoustic sensor with high spatial resolution (centimeter level), is helpful to monitor and locate the occurrence and development of structural perturbations in the material under the action of fluid.

SUMMARY

The purpose of the present disclosure is to at least partly overcome the defects of the prior art, and provide a multi-physical field imaging method based on PET-CT and DAS and a multi-physical field imaging system based on PET-CT and DAS.

In an embodiment, the present disclosure provides a multi-physical field imaging method and system based on PET-CT and DAS, which can directly image the fluid-solid coupling process in the material.

In an embodiment, the present disclosure provides a multi-physical field imaging method and system based on PET-CT and DAS, so that the imaging of the fluid-solid coupling process in the material is accurate and reliable.

In an embodiment, the present disclosure provides a multi-physical field imaging method and system based on PET-CT and DAS, which can make up for the deficiency of the research methods for studying the whole process of fluid-solid coupling of materials in natural science research.

In order to achieve the above-mentioned embodiments, the technical solutions of the present disclosure are as follows:

A multi-physical field imaging method based on PET-CT and DAS, for studying a dynamic fluid-solid coupling effect in non-metallic material, to study hydraulic fracturing process and earthquake induced by the hydraulic fracturing process, comprising:

Step A: wrapping distributed acoustic sensors on a surface of a non-metallic sample to be tested, and then placing the non-metallic sample to be tested and the distributed acoustic sensors in a pressure device; wherein the distributed acoustic sensors are phase-sensitive optical frequency domain reflectometers, made of silicon dioxide, the phase-sensitive optical frequency domain reflectometers are configured to have a spatial resolution of 10 cm, a strain resolution of $1n\varepsilon/\sqrt{Hz}$, and a vibration sampling frequency of 300 Hz, so as to obtain internal dynamic vibration signals generated from the fluid-solid coupling effect of the non-metallic samples to be tested; wherein the pressure device is made of a composite material of polyether ether ketone and carbon fiber, and the composite material is made from pure polyether ether ketone material filled with 40% by weight carbon fiber;

Step B: utilizing electric metering pumps remotely controlled by a computer to load triaxial pressures on the non-metallic sample to be tested, according to requirement of a research experiment, simulating different mechanical conditions to monitor interaction process between fluid and solid and physical response under different mechanical scenarios; wherein experimenters set pressures of the electric metering pumps remotely through the computer outside a PET/CT equipment room, according to the requirement of the experiment, and record pressure changes in real time;

Step C: preparing a tracer fluid, and diluting the tracer fluid;

Step D: pumping the diluted tracer fluid into the non-metallic sample to be tested through a metering pump remotely controlled by a computer;

Step E: continuously and in-situ collecting PET images and CT images of internal structure of the non-metallic sample to be tested; meanwhile, monitoring internal acoustic emission events of the non-metallic sample to be tested by using distributed acoustic sensors in real time;

Step F: combining the continuously-obtained PET images with the continuously-obtained CT images, to obtain PET/CT images;

Step G: analyzing data from monitoring of the distributed acoustic sensors, locating the acoustic emission events, and obtaining occurrence time and spatial location of internal perturbations of the non-metallic sample to be tested; and Step H: combining continuous in-situ dynamic PET/CT images with locating results of the acoustic emission events, to analyze a mechanism of fluid-solid coupling effect in the non-metallic sample to be tested under loaded stress; projecting spatial location information of the acoustic emission events to three-dimensional PET/CT images, to analyze a fluid-solid coupling process in the non-metallic sample to be tested.

According to some embodiments of the present disclosure, in the Step A, the distributed acoustic sensors are equidistantly wrapped on the surface of the non-metallic sample to be tested.

According to some embodiments of the present disclosure, the pressure device is a pressure device through which positrons and X-rays are able to penetrate.

According to some embodiments of the present disclosure, the tracer fluid is a positron tracer fluid.

According to another aspect of the present disclosure, there is provided a multi-physical field imaging system based on PET-CT and DAS, wherein the system is configured to implement the multi-physical field imaging method based on PET-CT and DAS according to any one of the preceding embodiments.

According to some embodiments of the present disclosure, the imaging system comprises:
  a PET machine, configured to scan electrons released by tracers in the non-metallic sample to be tested to obtain internal images of the non-metallic sample to be tested;
  a CT machine, configured for obtaining CT images of the non-metallic sample to be tested;
  a distributed acoustic sensing and monitoring system, connected to the distributed acoustic sensors and configured for analyzing obtained acoustic emission monitoring data, picking up data variation points for acoustic emission locating, obtaining spatiotemporal information of the acoustic emission events, and imaging the internal structure of the non-metallic sample to be tested;
  the pressure device, configured for accommodating the non-metallic sample to be tested and applying pressure to the non-metallic sample to be tested;
  an electric metering pump configured for applying confining pressure, an electric metering pump configured for applying axial pressure, and an electric metering pump configured for providing tracer; and
  a pressure loading control system, connected to the electric metering pump configured for applying confining pressure, the electric metering pump configured for applying axial pressure, and the electric metering pump configured for providing tracer.

According to some embodiments of the present disclosure, the pressure device comprises:
  a holder body, configured to accommodate the non-metallic sample to be tested;
  a first end cover and a second end cover, respectively arranged on two ends of the holder body;
  a confining pressure injection port, arranged in at least one of the first end cover and the second end cover;
  an axial pressure injection port, arranged in at least one of the first end cover and the second end cover;
  a tracer injection port, arranged in the holder body; and
  a pressure transmission core rod, arranged between the first end cover and the second end cover and configured to apply axial pressure to the non-metallic sample to be tested.

The beneficial effects of the present disclosure are as follows: A disruption experiment can be carried out by a pressure device under the condition of PET/CT continuous in-situ dynamic scanning, and a continuous acoustic emission event monitoring can be performed by the assistance of distributed acoustic sensing and monitoring system. On the one hand, the images of the internal structure and state of the non-metallic sample to be tested, under loaded stress during the fluid-solid coupling effect, may be obtained by PET/CT scanning; on the other hand, the occurrence time and location information of structural perturbations can be obtained through acoustic emission tomography. The information obtained from the monitoring of the above two physical fields is combined and analyzed, and the fluid-solid coupling effect can be analyzed from the perspective of multiple physical parameters. The multi-physical field imaging method and system based on PET-CT and DAS of the present disclosure can directly image the fluid-solid coupling process in the material, and the imaging is more accurate and reliable, making up for the deficiency of the research methods for studying the whole process of fluid-solid coupling of materials in natural science research.

DETAILED DESCRIPTION OF EMBODIMENTS

Figure 1:
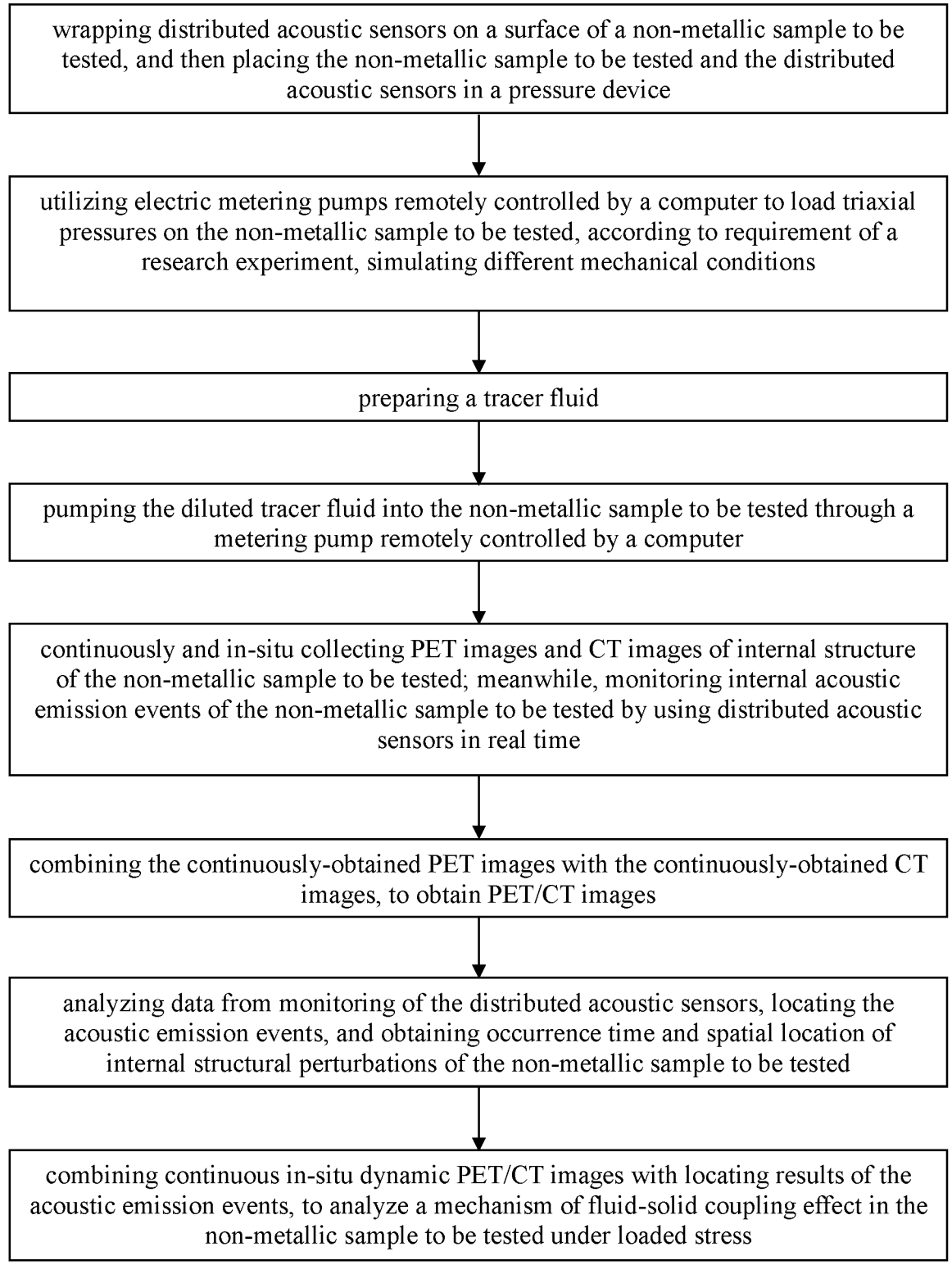
FIG. 1 is a flowchart of a multi-physical field imaging method based on PET-CT and DAS according to an embodiment of the present disclosure.

In order to make the above objectives, features, and advantages of the present disclosure more understandable, the present disclosure will be described in further detail below with reference to the accompanying drawings and the specific embodiments.

Fluid-solid effect is of great significance in the fields of aviation, aerospace, ocean, hydraulic engineering, civil engineering, petroleum, chemical industry and biology. The present disclosure focuses on the monitoring of the process of interaction between fluid and solid and the physical response under different mechanical scenarios.

Aiming at the problem that the traditional interior active source ultrasonic tomography technology and acoustic emission tomography technology cannot perform accurate dynamic imaging of the fluid-solid coupling process in the material, the present disclosure provides a multi-physical field imaging method and system based on PET/CT (or PET-CT) and DAS, that relates to an imaging device and a monitoring system. Their function lies in: utilizing PET/CT to directly perform high-resolution in-situ dynamic imaging of the fluid-solid coupling process in non-metallic material under the action of fluid under laboratory condition, and utilizing distributed acoustic sensors (DAS) of the phase-sensitive optical frequency domain reflectometers (d)-OFDR) to perform indirect imaging of the generation process of structural perturbations in the non-metallic material under the action of fluid-solid coupling. PET/CT scanning technology helps to study the path and process of fluid migration in the material, and DAS monitoring technology helps to study the acoustic emission response generated in the material under the action of fluid. Any single technical means is not enough to support an in-depth study of the mechanism of the fluid-solid coupling effect. The focus of the present disclosure is to integrate PET/CT scanning technology with high-resolution DAS monitoring technology, and to combine the flow process of the fluid in the material with the acoustic emission response when the internal structural perturbation of the material occurs under the action of fluid, so as to carry out the research of the mechanism of fluid-solid coupling effect.

Distributed Acoustic Sensing (DAS) technology is an emerging data acquisition technology that has developed rapidly in recent years. DAS generally consists of a demodulator (including an optical system and a signal acquisition system) and a normal optical fiber or a special optical fiber for sensing. DAS realizes the measurement of strain signal along the axial direction of the optical fiber by detecting a phase change of Rayleigh backward scattering light generated by the laser pulse in the internal scatterer of the optical fiber.

The existence of fluid significantly changes the physical and chemical properties of the material, and the real-time flow path of the fluid in the material cannot be obtained in previous studies. PET technology has a high time resolution and is highly sensitive to small changes in tracer concentration, therefore it is suitable for studying the dynamic flow process of the fluid in the material. The spatial resolution of PET imaging technology is limited, but this can be compensated by CT technology. The combination of PET technology and CT technology can perform more comprehensive imaging of the interior of the material, provide three-dimensional visual imaging of the dynamic fluid flow process, and help to study the flow mechanism.

Under the continuous action of the fluid, the stability of the internal structure of the material will be perturbed microscopically, and a series of disruptions will occur macroscopically. When the fluid-solid coupling effect occurs in the material, different degrees of acoustic emission responses will be produced. By deploying sensors in the field, researchers can monitor the fluid-solid coupling process in the target area for seismic monitoring, can realize early warning of disruption and locate the specific location of the disruption due to fluid action. In the present disclosure, the acoustic emission response generated by the fluid-solid coupling effect in a small-scale material can be monitored in the laboratory, so as to find the position of perturbations in the sample to be tested due to the interaction between the fluid and the solid. The phase-sensitive optical frequency domain reflectometer (d)-OFDR) technology monitors the vibration along the optical fiber by transmitting continuous optical pulse train signals with high coherence linear sweep, and the Rayleigh backward scattering light returned from the sensing optical fiber and the reference light perform beat frequency. The vibration event information can be obtained from demodulation of the differential phase change of the complex Rayleigh backward scattering profile, and the dynamic vibration signal generated by the fluid-solid coupling effect in the sample to be tested can be obtained. With the characteristics of the non-metallic material (radiation can penetrate through it and it will not interfere with the positron scanning) and high spatial resolution of the optical fiber, it can be wrapped on the surface of the sample to be tested for acoustic emission monitoring of the fluid-solid coupling process, without detrimental effect on PET/CT scanning imaging.

The in-situ dynamic PET/CT scanning image can directly reveal the dynamic process of the fluid-solid coupling effect in the sample to be tested, and it can monitor the acoustic emission events generated in the process of fluid-solid coupling by the distributed acoustic sensing technology, thereby indirectly obtaining occurrence time and location of perturbations in the non-metallic sample to be tested due to the fluid-solid coupling effect. Combining the directly-acquired in-situ dynamic PET/CT scanning images with the indirectly-acquired location information of the internal perturbations of the sample to be tested, it can analyze the changes in the internal state of the sample to be tested under the action of fluid and summarize the mechanism of fluid-solid coupling, thereby making up for the deficiency of the research methods for studying the whole process of fluid-solid coupling of materials in natural science research Based on the above-mentioned inventive concept, the multi-physical field imaging method based on PET-CT and DAS according to specific embodiments of the present disclosure includes:

Step A: wrapping distributed acoustic sensors equidistantly on the surface of the non-metallic sample to be tested, and then placing the non-metallic sample to be tested and the distributed acoustic sensors in a pressure device. Herein, the distributed acoustic sensors are preferably phase-sensitive optical frequency domain reflectometers (d)-OFDR), and the pressure device is a pressure device through which positrons and X-rays are able to penetrate, so as not to affect PET/CT imaging. Specifically, the pressure device is made of a composite material of polyether ether ketone and carbon fiber, and the composite material is made from pure polyether ether ketone material filled with 40% by weight carbon fiber.

Step B: utilizing high-precision electric metering pumps remotely controlled by a computer to load triaxial pressures on the non-metallic sample to be tested, according to requirement of a research experiment, simulating different mechanical conditions.

Step C: preparing a tracer fluid (generally a positron tracer fluid), and diluting the tracer fluid.

Step D: pumping the tracer fluid into the non-metallic sample to be tested through a high-precision metering pump remotely controlled by a computer;

Step E: during the whole experiment, continuously and in-situ collecting PET images and CT images of internal structure of the non-metallic sample to be tested; meanwhile, monitoring internal acoustic emission events of the non-metallic sample to be tested by using distributed acoustic sensors in real time.

Step F: combining the continuously-obtained PET images with the continuously-obtained CT images, to obtain PET/CT images.

Step G: analyzing data from monitoring of the distributed acoustic sensors, locating the acoustic emission events, and obtaining occurrence time and spatial location of internal perturbations of the non-metallic sample to be tested.

Step H: combining continuous in-situ dynamic PET/CT images with locating results of the acoustic emission events, to analyze a mechanism of fluid-solid coupling effect in the non-metallic sample to be tested under loaded stress.

In the Step A, the distributed acoustic sensors are equidistantly wrapped on the surface of the non-metallic sample to be tested. Obviously, wrapping the distributed acoustic sensors equidistantly is beneficial for subsequent data analysis.

The distributed acoustic sensors adopt phase-sensitive optical frequency domain reflectometers, made of silicon dioxide, the phase-sensitive optical frequency domain reflectometers are configured to have a spatial resolution of 10 cm, a strain resolution of $1n\varepsilon/\sqrt{Hz}$, and a vibration sampling frequency of 300 Hz. The phase-sensitive optical frequency domain reflectometers made of silicon dioxide do not produce artifacts on PET/CT scanning images and do not affect PET/CT imaging.

According to another aspect of the present disclosure, there is provided a multi-physical field imaging system based on PET-CT and DAS, wherein the system is configured to implement the multi-physical field imaging method based on PET-CT and DAS according to any one of the preceding embodiments.

Figure 2:
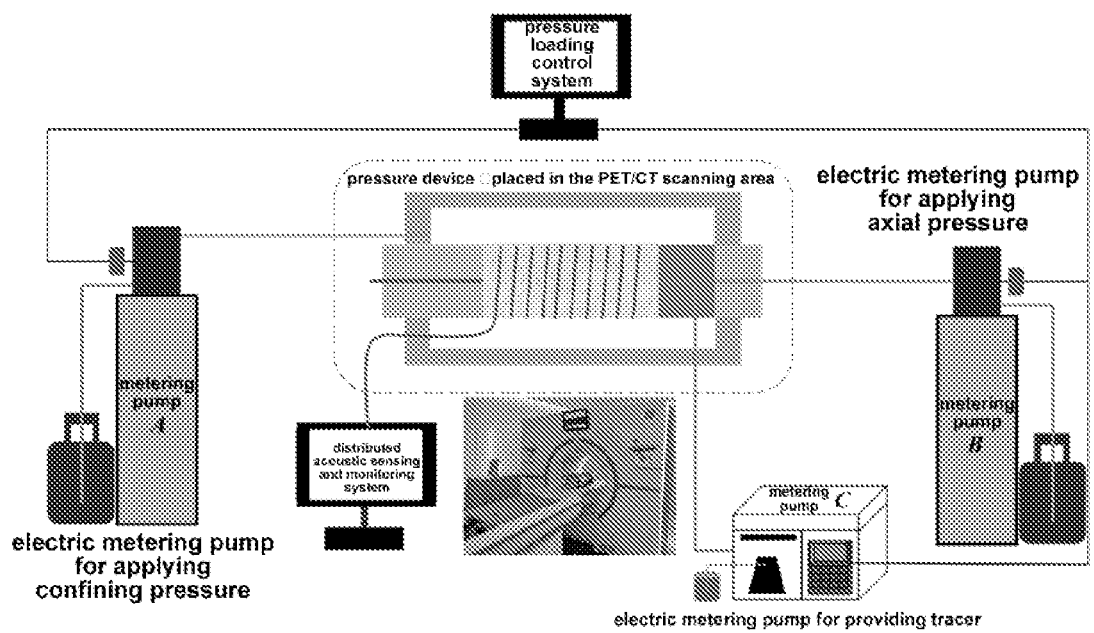
FIG. 2 is a schematic diagram of a multi-physical field imaging system based on PET-CT and DAS according to an embodiment of the present disclosure.

As shown in FIG. 2, the imaging system includes:
a PET machine, configured to scan electrons released by tracers in the non-metallic sample to be tested to obtain internal images of the non-metallic sample to be tested;
a CT machine, configured for obtaining CT images of the non-metallic sample to be tested;
a distributed acoustic sensing and monitoring system, connected to the distributed acoustic sensors and configured for analyzing obtained acoustic emission monitoring data, picking up data variation points for acoustic emission locating, obtaining spatiotemporal information of the acoustic emission events, and imaging the internal structure of the non-metallic sample to be tested;
the pressure device, configured for accommodating the non-metallic sample to be tested and applying pressure to the non-metallic sample to be tested;
an electric metering pump configured for applying confining pressure, an electric metering pump configured for applying axial pressure, and an electric metering pump configured for providing tracer, wherein they are all connected to the pressure device to apply pressure or tracer to the non-metallic sample to be tested; and
a pressure loading control system, connected to the electric metering pump configured for applying confining pressure, the electric metering pump configured for applying axial pressure, and the electric metering pump configured for providing tracer; the pressure loading control system being configured to control each electric metering pump, to control the pressure applied to the non-metallic sample to be tested and the loaded tracer provided to the non-metallic sample to be tested.

During the implementation of the experiment, the pressure device was placed in the PET/CT scanning area.

Figure 3:
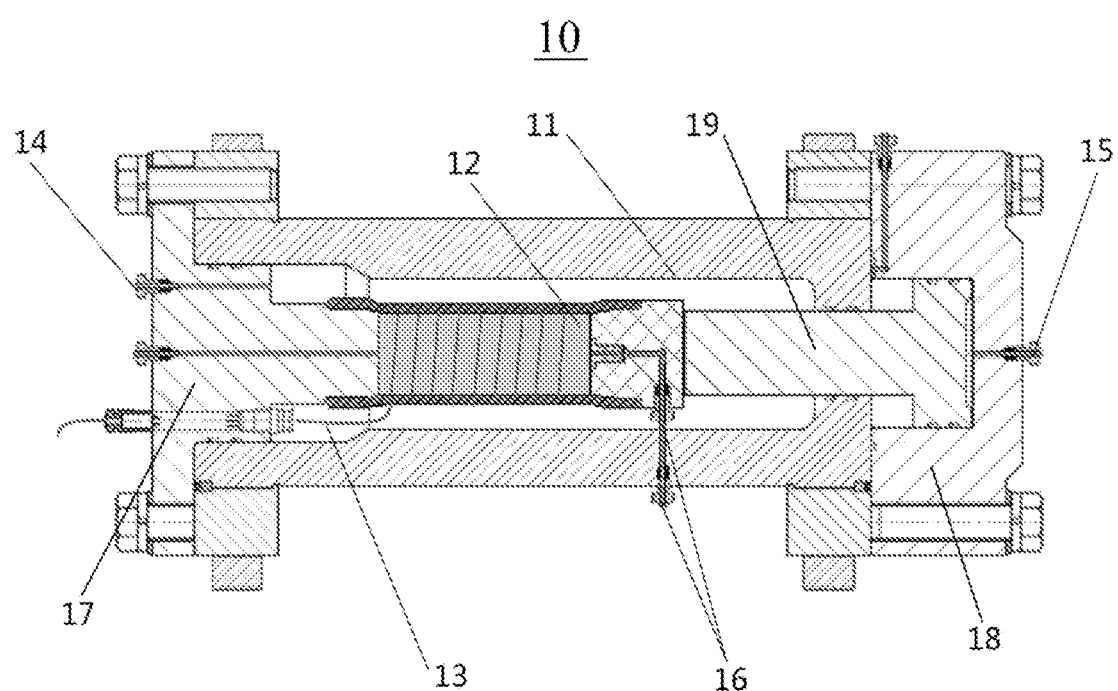
FIG. 3 is a pressure device of a schematic diagram of a multi-physical field imaging system based on PET-CT and DAS according to an embodiment of the present disclosure.

FIG. 3 shows a specific form of the pressure device of the imaging system, as shown in FIG. 3, the pressure device 10 includes:
a holder body 11, configured to accommodate the non-metallic sample 12 to be tested; during the experiment, the distributed acoustic sensor 13 being wrapped on the surface of the non-metallic sample 12 to be tested and accommodated in the holder body 11 together;
a first end cover 17 and a second end cover 18, respectively arranged on two ends of the holder body 11; the holder body 11 being cylindrical, the first end cover 17 and the second end cover 18 being connected and fastened to the end of the holder body 11 by bolts and flanges;
a confining pressure injection port 14, arranged in the first end cover 17 or the second end cover 18 and configured to control the confining pressure acting on the non-metallic sample 12 to be tested;
an axial pressure injection port 15, arranged in the first end cover 17 or the second end cover 18, or arranged in the first end cover 17 and the second end cover 18, and configured to control the axial pressure acting on the non-metallic sample 12 to be tested;
a tracer injection port 16, arranged in the holder body 11, the tracer injection port 16 being connected with the non-metallic sample 12 to be tested through a pipeline, and being configured to supply the tracer fluid to the non-metallic sample 12 to be tested; and
a pressure transmission core rod 19, arranged between the first end cover 17 and the second end cover 18 and configured to apply axial pressure to the non-metallic sample to be tested.

The pressure device herein is just an example, and the pressure device may have other variations without affecting the implementation of the multi-physical field imaging method based on PET-CT and DAS of the present disclosure.

In the present disclosure, during the process of gradually producing structural perturbations to the sample to be tested, the tracer fully enters the disrupted parts, and the positrons released by the tracer in the sample to be tested are scanned by means of the PET machine, to obtain an image of the local area of the disrupted part. The CT machine is used for high-precision positioning and combination of the PET images. Compared with single CT scanning, PET/CT scanning can not only shorten the data acquisition time, but also greatly improve the image resolution, capturing the mesoscopic structure of internal perturbation that is not easy to image in the single CT scanning.

The PET images and CT images of the sample to be tested are taken continuously, and after the multiple sets of image are combined, it can obtain the PET/CT images. It can perform real-time dynamic imaging of the generation process of the structural perturbation according to the tracer fluid migration path in the sample to be tested. In order to reduce the radiation exposure of the experimenters as much as possible, all the pressure injection pumps used in the whole experiment process are electric metering pumps that can be controlled by a remote computer. The experimenter can set the pressure of the metering pump remotely through the computer outside the PET/CT equipment room, according to the requirement of the experiment, and record the pressure changes in real time.

Acoustic emission monitoring has always been a main analysis method to monitor the internal perturbation process of the sample during the experiment. Because the conventional acoustic emission detector contains metal components (radiation cannot penetrate and will interfere with the scanning of positrons), if it is pasted on the surface of the sample to be tested for PET/CT scanning. The existence of metal components will cause artifacts on the scanning image, which is harmful to the PET/CT imaging. The present disclosure adopts distributed acoustic sensors made of silicon dioxide to replace the conventional acoustic emission probe, the distributed acoustic sensors will not affect PET/CT scanning results while meeting the acoustic emission monitoring requirements during the experiment. The phase-sensitive optical frequency domain reflectometer (d)-OFDR) used in the present disclosure has a spatial resolution of 10 cm, a strain resolution of $1n\varepsilon/\sqrt{Hz}$, and a vibration sampling frequency of 300 Hz, fully meeting the acoustic emission monitoring requirements in the experiment.

After the experiment is finished, the acquired acoustic emission monitoring data is analyzed, the data mutation points are picked up for acoustic emission locating, the spatiotemporal information of the acoustic emission events is obtained, and then the internal structure of the sample to be tested is imaged. The spatial location information of the acoustic emission events is projected into the three-dimensional PET/CT images, to analyze a fluid-solid coupling process in the non-metallic sample to be tested.

The container used to accommodate the sample to be tested is a pressure device that is resistant to high pressure and easily penetrated by positrons/X-rays. The body of the pressure device is made of a composite material of polyether ether ketone and carbon fiber. The material is a special polymer material, which is reinforced by filling 40% by weight of carbon fiber to pure polyether ether ketone material, so that the composite material has a higher elastic modulus, better mechanical strength and higher creep resistance, therefore the pressure device can withstand high pressure and high temperature conditions. The constituent elements of this material only contain three low atomic number elements of hydrogen, oxygen and carbon, so the density is very low, only 1.45 $g/cm^{-3}$. X-rays have less attenuation when penetrating low atomic number and low density materials, so the use of this material will not have adverse effects on CT images and PET-CT images. Therefore the present disclosure adopts this material to make the body of the pressure device.

The beneficial effects of the present disclosure are as follows: A disruption experiment can be carried out by a pressure device under the condition of PET/CT continuous in-situ dynamic scanning, and a continuous acoustic emission event monitoring can be performed by the assistance of distributed acoustic sensing and monitoring system. On the one hand, the images of the internal structure and state of the non-metallic sample to be tested, under loaded stress during the fluid-solid coupling effect, may be obtained by PET/CT scanning; on the other hand, the occurrence time and location information of the perturbations can be obtained through acoustic emission tomography. The information obtained from the monitoring of the above two physical fields is combined and analyzed, and the fluid-solid coupling effect can be analyzed from the perspective of multiple physical parameters. The multi-physical field imaging method and system based on PET-CT and DAS of the present disclosure can directly image the fluid-solid coupling process in the material, and the imaging is more accurate and reliable, making up for the deficiency of the research methods for studying the whole process of fluid-solid coupling of materials in natural science research.

While the embodiments of the present disclosure have been shown and described above, it is to be understood that the above embodiments are illustrative and are not to be construed as limiting the scope of the present disclosure. Changes, modifications, substitutions and variations may be made to the above embodiments by those skilled in the art within the scope of the present disclosure.

LIST OF REFERENCE NUMERALS

10 pressure device
11 holder body
12 Non-metallic sample to be tested
13 Distributed Acoustic Sensor
14 Confining pressure injection port
15 Axial pressure injection port
16 Tracer injection port
17 First end cover
18 Second end cover
19 Pressure transmission core rod.

What is claimed is:

1. A multi-physical field imaging method based on positron emission tomography-computed tomography (PET-CT) and directed acoustic sensing (DAS), for studying a dynamic fluid-solid coupling effect in non-metallic material, to study hydraulic fracturing processes comprising:

Step A: wrapping distributed acoustic sensors on a surface of a non-metallic sample to be tested, and then placing the non-metallic sample to be tested and the distributed acoustic sensors in a pressure device; wherein the distributed acoustic sensors are phase-sensitive optical frequency domain reflectometers, made of silicon dioxide, the phase-sensitive optical frequency domain reflectometers are configured to have a spatial resolution of 10 cm, a strain resolution of 1nε/√Hz, and a vibration sampling frequency of 300 Hz, so as to obtain internal dynamic vibration signals generated from the fluid-solid coupling effect of the non-metallic samples to be tested; the pressure device is made of a composite material of polyether ether ketone filled with 40% by weight carbon fiber;

Step B: utilizing electric metering pumps remotely controlled by a computer configured to load triaxial pressures on the non-metallic sample to be tested, performing different mechanical conditions to monitor interaction process between fluid and solid and the sample's physical response, setting pressures of the electric metering pumps remotely through the computer according to the requirement of the experiment, and recording pressure changes in real time;

Step C: preparing a tracer fluid, and diluting the tracer fluid;

Step D: pumping the diluted tracer fluid into the non-metallic sample to be tested through a metering pump remotely controlled by the computer;

Step E: continuously and in-situ collecting PET images and CT images of internal structure of the non-metallic sample to be tested; meanwhile, monitoring internal acoustic emission events of the non-metallic sample to be tested by using distributed acoustic sensors in real time;

Step F: combining the continuously-obtained PET images with the continuously-obtained CT images, to obtain PET/CT images;

Step G: analyzing data from monitoring of the distributed acoustic sensors, locating the acoustic emission events, and obtaining occurrence time and spatial location of internal structural perturbation of the non-metallic sample to be tested; and Step H: combining continuous in-situ dynamic PET/CT images with locating results of the acoustic emission events, to analyze a mechanism of fluid-solid coupling effect in the non-metallic sample to be tested under loaded stress; projecting spatial location information of the acoustic emission events to three-dimensional PET/CT images, to analyze a fluid-solid coupling process in the non-metallic sample to be tested.

2. A multi-physical field imaging system based on PET-CT and DAS, wherein the system is configured to implement the multi-physical field imaging method based on PET-CT and DAS according to claim 1.

3. The multi-physical field imaging system based on PET-CT and DAS according to claim 2, wherein the imaging system comprises:
a PET machine, configured to scan electrons released by tracers in the non-metallic sample to be tested to obtain internal images of the non-metallic sample to be tested;
a CT machine, configured for obtaining CT images of the non-metallic sample to be tested;
a distributed acoustic sensing and monitoring system, connected to the distributed acoustic sensors and configured for analyzing obtained acoustic emission monitoring data, picking up data variation points for acoustic emission locating, obtaining spatiotemporal information of the acoustic emission events, and imaging the internal structure of the non-metallic sample to be tested;
the pressure device, configured for accommodating the non-metallic sample to be tested and applying pressure to the non-metallic sample to be tested;
an electric metering pump configured for applying confining pressure, an electric metering pump configured for applying axial pressure, and an electric metering pump configured for providing tracer; and
a pressure loading control system, connected to the electric metering pump configured for applying confining pressure, the electric metering pump configured for applying axial pressure, and the electric metering pump configured for providing tracer.

4. The multi-physical field imaging system based on PET-CT and DAS according to claim 3, wherein the pressure device comprises:
a holder body, configured to accommodate the non-metallic sample to be tested;
a first end cover and a second end cover, respectively arranged on two ends of the holder body;
a confining pressure injection port, arranged in at least one of the first end cover and the second end cover;
an axial pressure injection port, arranged in at least one of the first end cover and the second end cover;
a tracer injection port, arranged in the holder body; and
a pressure transmission core rod, arranged between the first end cover and the second end cover and configured to apply axial pressure to the non-metallic sample to be tested.

5. The multi-physical field imaging method based on PET-CT and DAS according to claim 1, wherein:
in the Step A, the distributed acoustic sensors are equidistantly wrapped on the surface of the non-metallic sample to be tested.

6. A multi-physical field imaging system based on PET-CT and DAS, wherein the system is configured to implement the multi-physical field imaging method based on PET-CT and DAS according to claim 5.

7. The multi-physical field imaging method based on PET-CT and DAS according to claim 5, wherein:
the pressure device is a pressure device through which positrons and X-rays are able to penetrate.

8. A multi-physical field imaging system based on PET-CT and DAS, wherein the system is configured to implement the multi-physical field imaging method based on PET-CT and DAS according to claim 7.

9. The multi-physical field imaging method based on PET-CT and DAS according to claim 7, wherein:
the tracer fluid is a positron tracer fluid.

10. A multi-physical field imaging system based on PET-CT and DAS, wherein the system is configured to implement the multi-physical field imaging method based on PET-CT and DAS according to claim 9.

* * * * *